US006451812B1

(12) United States Patent
End et al.

(10) Patent No.: US 6,451,812 B1
(45) Date of Patent: Sep. 17, 2002

(54) FARNESYL PROTEIN TRANSFERASE INHIBITORS FOR TREATING ARTHROPATHIES

(75) Inventors: David William End, Ambler, PA (US); Marina Lucie Louise Cools, Retie; Jean Pierre Frans Van Wauwe, Beerse, both of (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/743,077

(22) PCT Filed: Jun. 30, 1999

(86) PCT No.: PCT/EP99/04546

§ 371 (c)(1),
(2), (4) Date: Jan. 3, 2001

(87) PCT Pub. No.: WO00/01386

PCT Pub. Date: Jan. 13, 2000

(30) Foreign Application Priority Data

Jul. 6, 1998 (EP) .............................................. 98202258

(51) Int. Cl.[7] .............................................. A61K 31/47
(52) U.S. Cl. ........................ 514/312; 514/311; 514/314
(58) Field of Search ................................ 514/312, 311, 514/314

(56) References Cited

U.S. PATENT DOCUMENTS

| 5,574,025 A | * | 11/1996 | Anthony |
| 5,602,184 A | | 2/1997 | Myers et al. |
| 6,037,350 A | * | 3/2000 | Venet |
| 6,150,377 A | * | 11/2000 | Lyssikatos |
| 6,169,096 B1 | * | 1/2001 | Venet |
| 6,187,786 B1 | * | 2/2001 | Venet |
| 6,307,101 B1 | * | 10/2001 | Campbell .................... 564/154 |

FOREIGN PATENT DOCUMENTS

| WO | WO 00/01411 | 1/1997 |
| WO | WO 97/16443 | 5/1997 |
| WO | 97/21701 | * 6/1997 |
| WO | WO 97/21701 | 6/1997 |
| WO | WO 97/38697 | 10/1997 |
| WO | WO 98/40383 | 9/1998 |
| WO | 98/40383 | * 9/1998 |
| WO | 98/43629 | * 10/1998 |
| WO | WO 98/43629 | 10/1998 |
| WO | WO 98/49157 | 11/1998 |
| WO | 98/55124 | * 12/1998 |
| WO | WO 98/55124 | 12/1998 |
| WO | WO 98/57959 | 12/1998 |
| WO | WO 00/01386 | 1/2000 |

OTHER PUBLICATIONS

Doll, CA 130:81411, 1998.*
Bernard et al., Cancer Research, vol. 56, Apr. 15, 1996, "The Farnesyltransferase Inhibitor FTI–277 Radiosensitizes H–ras–transformed Rat Embryo Fibroblasts," pp. 1727–1730.
Rak et al., Cancer Research, vol. 55, Oct. 15, 1995, "Mutant ras Oncogenes Upregulate VEGF/VPF Expression: Implications for Induction and Inhibition of Tumor Angiogenesis," pp. 4575–4580.
Doll, CA 130:81411, 1998.

* cited by examiner

Primary Examiner—D. Margaret Seaman
(74) Attorney, Agent, or Firm—Myra McCormack

(57) ABSTRACT

The present invention is concerned with the finding that farnesyl protein transferase inhibitors are useful for preparing a pharmaceutical composition for treating arthropathies such as rheumatoid arthritis, osteoarthritis, juvenile arthritis, and gout.

11 Claims, No Drawings

FARNESYL PROTEIN TRANSFERASE INHIBITORS FOR TREATING ARTHROPATHIES

CROSS REFERENCE TO RELATED APPLICATIONS

This application is the National Stage application under 35 U.S.C. §371 of International Application No. PCT/EP99/04546 filed Jun. 30, 1999, which claims priority from EP99202258.4, filed Jul. 6, 1998, the contents of all of which are hereby incorporated by reference.

The present invention is concerned with the finding that farnesyl protein transferase inhibitors are useful for preparing a pharmaceutical composition for treating arthropathies such as, for example, rheumatoid arthritis, osteoarthritis, juvenile arthritis, and gout.

In Arthritis and Rheumatism, 40 (9), 1997, 1636–1643, Roivanen et al. describe H-ras oncogene point mutations in arthritic (and in healthy) synovium. Mutations in codon 13 and unexpectedly also in codon 14 could be detected in arthritic synovia from patients with rheumatoid arthritis, osteoarthritis and other arthropathies, but also in the synovia of controls without any joint disease. Whether the mutations have any importance in the pathogenesis of joint diseases therefore remains unanswered.

WO-97/21701 describes the preparation, formulation and pharmaceutical properties of farnesyl protein transferase inhibiting (imidazoly-5-yl)methyl-2-quinolinone derivatives of formulas (I), (II) and (III), as well as intermediates of formula (II) and (III) that are metabolized in vivo to the compounds of formula (I). The compounds of formulas (I), (II) and (III) are represented by

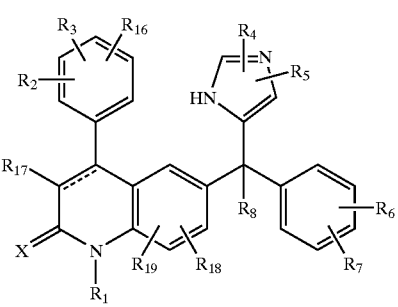
(I)

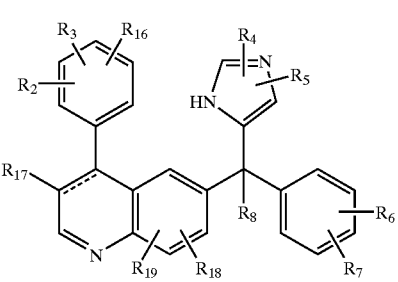
(II)

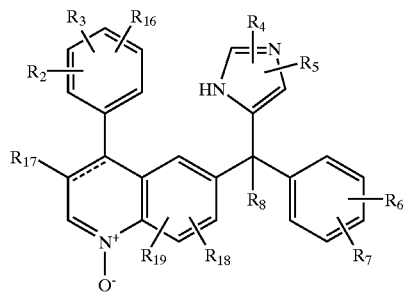
(III)

the pharmaceutically acceptable acid or base addition salts and the stereochemically isomeric forms thereof, wherein the dotted line represents an optional bond;

X is oxygen or sulfur;

$R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl, or a radical of formula $-Alk^1-C(=O)-R^9$, $-Alk^1-S(O)-R^9$ or $-Alk^1-S(O)_2-R^9$, wherein $Alk^1$ is $C_{1-6}$alkanediyl, $R^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;

$R^2$, $R^3$ and $R^{16}$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino$C_{1-6}$alkyl-oxy, mono- or di($C_{1-6}$alkyl)amino$C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl, 4,4-dimethyloxazolyl; or when on adjacent positions $R^2$ and $R^3$ taken together may form a bivalent radical of formula

| | |
|---|---|
| $-O-CH_2-O-$ | (a-1), |
| $-O-CH_2-CH_2-O-$ | (a-2), |
| $-O-CH=CH-$ | (a-3), |
| $-O-CH_2-CH_2-$ | (a-4), |
| $-O-CH_2-CH_2-CH_2-$ | (a-5), | or

| | |
|---|---|
| $-CH=CH-CH=CH-$ | (a-6); |

$R^4$ and $R^5$ each independently are hydrogen, halo, $Ar^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2C_{1-6}$alkyl;

$R^6$ and $R^7$ each independently are hydrogen, halo, cyano, $C_{1-6}$alkyl, $C_{1-6}$alkyloxy, $Ar^2$oxy, trihalomethyl, $C_{1-6}$alkylthio, di($C_{1-6}$alkyl)amino, or when on adjacent positions $R^6$ and $R^7$ taken together may form a bivalent radical of formula

| | |
|---|---|
| $-O-CH_2-O-$ | (c-i), | or

| | |
|---|---|
| $-CH=CH-CH=CH-$ | (c-2); |

$R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyano$C_{1-6}$alkyl, $C_{1-6}$alkyloxycarbonyl$C_{1-6}$alkyl, carboxy$C_{1-6}$alkyl, hydroxy$C_{1-6}$alkyl, amino$C_{1-6}$alkyl, mono- or di($C_{1-6}$ alkyl)-amino$C_{1-6}$alkyl, imidazolyl, halo$C_{1-6}$alkyl, $C_{1-6}$alkyloxy$C_{1-6}$alkyl, aminocarbonyl$C_{1-6}$alkyl, or a radical of formula —O—$R^{10}$ (b-1), —S—$R^{10}$ (b-2), —N—$R^{11}R^{12}$ (b-3), wherein
$R^{10}$ is hydrogen, $C_{1-6}$alkyl, $C_{1-6}$alkylcarbonyl, $Ar^1$, $Ar^2C_{1-6}$alkyl, $C_{1-6}$alkyloxycarbonyi$C_{1-6}$alkyl, or a radical or formula -Alk$^2$-O$R^{13}$ or -Alk$^2$-N$R^{14}R^{15}$;
$R^{11}$ is hydrogen, $C_{1-12}$alkyl, $Ar^1$ or $Ar^2C_{1-6}$alkyl;
$R^{12}$ is hydrogen, $C_{1-6}$alkyl, $C_{1-6}$alkylcarbonyl, $C_{1-6}$alkyloxycarbonyl, $C_{1-6}$alkylaminocarbonyl, $Ar^1$, $Ar^2C_{1-6}$alkyl, $C_{1-6}$alkylcarbonyl-$C_{1-6}$alkyl, a natural amino acid, $Ar^1$carbonyl, $Ar^2C_{1-6}$alkylcarbonyl, aminocarbonyicarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical or formula -Alk$^2$-O$R^{13}$ or -Alk$^2$-N$R^{14}R^{15}$;
wherein
Alk$^2$ is $C_{1-6}$alkanediyl;
$R^{13}$ is hydrogen, $C_{1-6}$alkyl, $C_{1-6}$alkylcarbonyl, hydroxy-$C_{1-6}$alkyl, $Ar^1$ or $Ar^2C_{1-6}$alkyl;
$R^{14}$ is hydrogen, $C_{1-6}$alkyl, $Ar^1$ or $Ar^2C_{1-6}$alkyl;
$R^{15}$ is hydrogen, $C_{1-6}$alkyl, $C_{1-6}$alkylcarbonyl, $Ar^1$ or $Ar^2C_{1-6}$alkyl;
$R^{17}$ is hydrogen, halo, cyano, $C_{1-6}$alkyl, $C_{1-6}$alkyloxycarbonyl, $Ar^1$;
$R^{18}$ is hydrogen, $C_{1-6}$alkyl, $C_{1-6}$alkyloxy or halo;
$R^{19}$ is hydrogen or $C_{1-6}$alkyl;
$Ar^1$ is phenyl or phenyl substituted with $C_{1-6}$alkyl, hydroxy, amino, $C_{1-6}$alkyloxy or halo; and
$Ar^2$ is phenyl or phenyl substituted with $C_{1-6}$alkyl, hydroxy, amino, $C_{1-6}$alkyloxy or halo.

WO-97/16443 concerns the preparation, formulation and pharmaceutical properties of farnesyl protein transferase inhibiting compounds of formula (IV), as well as intermediates of formula (V) and (VI) that are metabolized in vivo to the compounds of formula (IV). The compounds of formulas (IV), (V) and (VI) are represented by

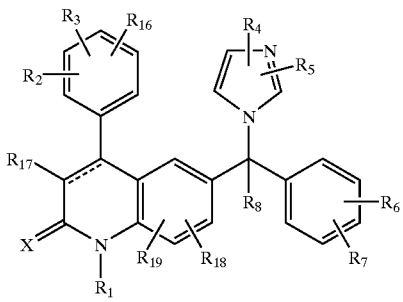

(IV)

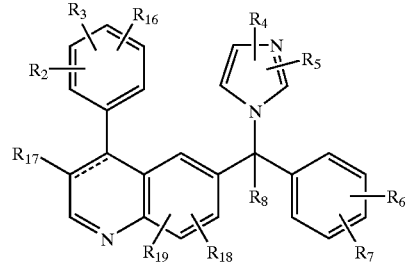

(V)

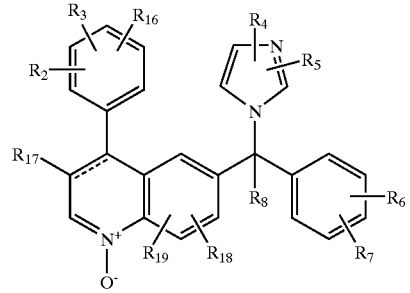

(VI)

the pharmaceutically acceptable acid or base addition salts and the stereochemically isomeric forms thereof, wherein the dotted line represents an optional bond;

X is oxygen or sulfur;
$R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl, or a radical of formula -Alk$^1$-C(=O)—$R^9$, -Alk$^1$-S(O)—$R^9$ or -Alk$^1$-S(O)$_2$—$R^9$,
wherein
Alk$^1$ is $C_{1-6}$alkanediyl,
$R^9$ is hydroxy, $C_{1-6}$alkyl, $C_{1-6}$alkyloxy, amino, $C_{1-8}$alkylamino or $C_{1-8}$galkylamino substituted with $C_{1-6}$alkyloxycarbonyl;
$R^2$ and $R^3$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino-$C_{1-6}$alkyloxy, mono- or di($C_{1-6}$alkyl)amino$C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl; or
when on adjacent positions $R^2$ and $R^3$ taken together may form a bivalent radical of formula —O—CH$_2$—O— (a-1), —O—CH$_2$—CH$_2$—O— (a-2), —O—CH=CH— (a-3), —O—CH$_2$—CH$_2$— (a-4), —O—CH$_2$—CH$_2$—CH$_2$— (a-5), or —CH=CH—CH=CH— (a-6);

$R^4$ and $R^5$ each independently are hydrogen, $Ar^1$, $C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2C_{1-6}$alkyl;

$R^6$ and $R^7$ each independently are hydrogen, halo, cyano, $C_{1-6}$alkyl, $C_{1-6}$alkyloxy or $Ar^2$oxy;

$R^8$ is hydrogen, $C_{1-6}$alkyl, cyano, hydroxycarbonyl, $C_{1-6}$alkyloxycarbonyl, $C_{1-6}$alkyl-carbonyl$C_{1-6}$alkyl, cyano$C_{1-6}$alkyl, $C_{1-6}$alkyloxycarbonyl$C_{1-6}$alkyl, hydroxy-carbonyl$C_{1-6}$alkyl, hydroxy$C_{1-6}$alkyl, amino$C_{1-6}$alkyl, mono- or di($C_{1-6}$alkyl)-amino$C_{1-6}$alkyl, halo$C_{1-6}$alkyl, $C_{1-6}$alkyloxy$C_{1-6}$alkyl, aminocarbonyl$C_{1-6}$alkyl, $Ar^1$, $Ar^2C_{1-6}$alkyloxy$C_{1-6}$alkyl, $C_{1-6}$alkylthio$C_{1-6}$alkyl;

$R^{10}$ is hydrogen, $C_{1-6}$alkyl, $C_{1-6}$alkyloxy or halo;

$R^{11}$ is hydrogen or $C_{1-6}$alkyl;

$Ar^1$ is phenyl or phenyl substituted with $C_{1-6}$alkyl, hydroxy, amino, $C_{1-6}$alkyloxy or halo;

$Ar^2$ is phenyl or phenyl substituted with $C_{1-6}$alkyl, hydroxy, amino, $C_{1-6}$alkyloxy or halo.

PCT/EP98/01296, filed Mar. 3, 1998, concerns the preparation, formulation and pharmaceutical properties of farnesyl protein transferase inhibiting compounds of formula (VII)

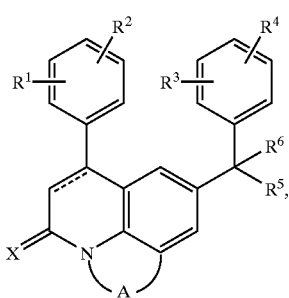

(I)

the pharmaceutically acceptable acid addition salts and the stereochemically isomeric forms thereof, wherein the dotted line represents an optional bond;

X is oxygen or sulfur;

—A— is a bivalent radical of formula

| —CH=CH— | (a-1), | —CH$_2$—S— | (a-6), |
| —CH$_2$—CH$_2$— | (a-2), | —CH$_2$—CH$_2$—S— | (a-7), |
| —CH$_2$—CH$_2$—CH$_2$— | (a-3), | —CH=N— | (a-8), |
| —CH$_2$—O— | (a-4), | —N=N— | (a-9), or |
| —CH$_2$—CH$_2$—O— | (a-5), | —CO—NH— | (a-10); | wherein optionally one hydrogen atom may be replaced by $C_{1-4}$alkyl or $Ar^1$;

$R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino$C_{1-6}$alkyloxy, $Ar^2$, $Ar^2$-$C_{1-6}$alkyl, $Ar^2$-oxy, $Ar^2$-$C_{1-6}$alkyloxy; or when on adjacent positions $R^1$ and $R^2$ taken together may form a bivalent radical of formula —CH$_2$—O— (b-1), —O—CH$_2$—CH$_2$—O— (b-2), —O—CH=CH— (b-3), —O—CH$_2$—CH$_2$— (b-4), —O—CH$_2$—CH$_2$—CH$_2$— (b-5), or —CH=CH—CH=CH— (b-6);

$R^3$ and $R^4$ each independently are hydrogen, halo, cyano, $C_{1-6}$alkyl, $C_{1-6}$alkyloxy, $Ar^3$-oxy, $C_{1-6}$alkylthio, di($C_{1-6}$alkyl)amino, trihalomethyl, trihalomethoxy, or when on adjacent positions $R^3$ and $R^4$ taken together may form a bivalent radical of formula —O—CH$_2$—O— (c-1), —O—CH$_2$—CH$_2$—O— (c-2), or —CH=CH—CH=CH— (c-3);

$R^5$ is a radical of formula

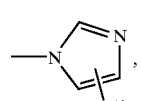

(d-1)

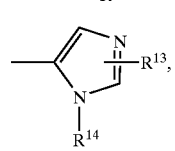

(d-2)

wherein $R^{13}$ is hydrogen, halo, $Ar^4$, $C_{1-6}$alkyl, hydroxy$C_{1-6}$alkyl, $C_{1-6}$alkyloxy-$C_{1-6}$alkyl, $C_{1-6}$alkyloxy, $C_{1-6}$alkylthio, amino, $C_{1-6}$alkyloxy-carbonyl, $C_{1-6}$alkylS(O)$C_{1-6}$alkyl or $C_{1-6}$alkylS(O)$_2C_{1-6}$alkyl;

$R^{14}$ is hydrogen, $C_{1-6}$alkyl or di($C_{1-4}$alkyl)aminosulfonyl;

$R^6$ is hydrogen, hydroxy, halo, $C_{1-6}$alkyl, cyano, halo$C_{1-6}$alkyl, hydroxy$C_{1-6}$alkyl, cyano$C_{1-6}$alkyl, amino$C_{1-6}$alkyl, $C_{1-6}$alkyloxy$C_{1-6}$alkyl, $C_{1-6}$alkylthio$C_{1-6}$alkyl, aminocarbonyl$C_{1-6}$alkyl, $C_{1-6}$alkyloxycarbonyl$C_{1-6}$alkyl, $C_{1-6}$alkylcarbonyl-$C_{1-6}$alkyl, $C_{1-6}$alkyloxycarbonyl, mono- or di($C_{1-6}$alkyl)amino$C_{1-6}$alkyl, $Ar^5$, $Ar^5$-$C_{1-6}$alkyloxy$C_{1-6}$alkyl; or a radical of formula —O—$R^7$ (e-1), —S—$R^7$ (e-2), —N—$R^8R^9$ (e-3), wherein $R^7$ is hydrogen, $C_{1-6}$alkyl, $C_{1-6}$alkylcarbonyl, $Ar^6$, $Ar^6$-$C_{1-6}$alkyl, $C_{1-6}$alkyloxycarbonyl$C_{1-6}$alkyl, or a radical of formula -Alk-OR$^{10}$ or -Alk-NR$^{11}R^{12}$;

$R^8$ is hydrogen, $C_{1-6}$alkyl, $Ar^7$ or $Ar^7$-$C_{1-6}$alkyl;

$R^9$ is hydrogen, $C_{1-6}$alkyl, $C_{1-6}$alkylcarbonyl, $C_{1-6}$alkyloxycarbonyl, $C_{1-6}$alkylaminocarbonyl, $Ar^8$, $Ar^8$-$C_{1-6}$alkyl, $C_{1-6}$alkylcarbonyl-$C_{1-6}$alkyl, $Ar^8$-carbonyl, $Ar^8$-$C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$ alkylcarbonyl, amino, $C_{1-6}$alkylamino, $C_{1-6}$alkylcarbonylamino, or a radical or formula -Alk-$OR^{10}$ or -Alk-$NR^{11}R^{12}$;
wherein
Alk is $C_{1-6}$alkanediyl;
$R^{10}$ is hydrogen, $C_{1-6}$alkyl, $C_{1-6}$alkylcarbonyl, hydroxy-$C_{1-6}$alkyl, $Ar^9$ or $Ar^9$-$C_{1-6}$alkyl;
$R^{11}$ is hydrogen, $C_{1-6}$alkyl, $C_{1-6}$alkylcarbonyl, $Ar^{10}$ or $Ar^{10}$-$C_{1-6}$alkyl;
$R^{12}$ is hydrogen, $C_{1-6}$alkyl, $Ar^{11}$ or $Ar^{11}$-$C_{1-6}$alkyl; and
$Ar^1$ to $Ar^{11}$ are each independently selected from phenyl; or phenyl substituted with halo, $C_{1-6}$alkyl, $C_{1-6}$alkyloxy or trifluoromethyl.

PCT/EP98/02357, filed Apr. 17, 1998, concerns the preparation, formulation and pharmaceutical properties of farnesyl protein transferase inhibiting compounds of formula (VIII)

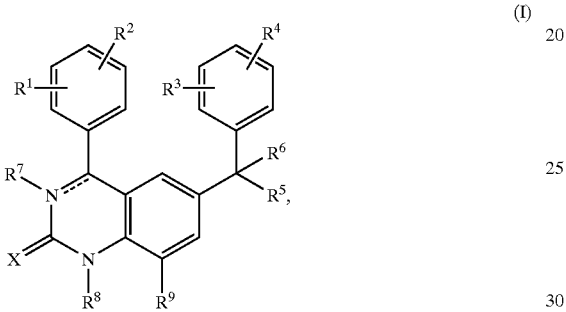

(I)

the pharmaceutically acceptable acid addition salts and the stereochemically isomeric forms thereof, wherein
the dotted line represents an optional bond;
X is oxygen or sulfur;
$R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino$C_{1-6}$alkyloxy, $Ar^1$, $Ar^1C_{1-6}$alkyl, $Ar^1$oxy or $Ar^1C_{1-6}$ alkyloxy;
$R^3$ and $R^4$ each independently are hydrogen, halo, cyano, $C_{1-6}$alkyl, $C_{1-6}$alkyloxy, $Ar^1$oxy, $C_{1-6}$alkylthio, di($C_{1-6}$alkyl)amino, trihalomethyl or trihalomethoxy;
$R^5$ is hydrogen, halo, $C_{1-6}$alkyl, cyano, halo$C_{1-6}$alkyl, hydroxy$C_{1-6}$alkyl, cyano$C_{1-6}$alkyl, amino$C_{1-6}$alkyl, $C_{1-6}$alkyloxy$C_{1-6}$alkyl, $C_{1-6}$alkylthio$C_{1-6}$alkyl, aminocarbonyl$C_{1-6}$alkyl, $C_{1-6}$alkyloxycarbonyl$C_{1-6}$alkyl, $C_{1-6}$alkylcarbonyl-$C_{1-6}$alkyl, $C_{1-6}$alkyloxycarbonyl, mono- or di($C_{1-6}$alkyl)amino $C_{1-6}$alkyl, $Ar^1$, $Ar^1C_{1-6}$alkyloxy$C_{1-6}$alkyl; or a radical of formula —O—$R^{10}$ (a-1),
—S—$R^{10}$ (a-2),
—N—$R^{11}R^{12}$ (a-3), wherein
$R^{10}$ is hydrogen, $C_{1-6}$alkyl, $C_{1-6}$alkylcarbonyl, $Ar^1$, $Ar^1C_{1-6}$alkyl, $C_{1-6}$alkyloxycarbonyl$C_{1-6}$alkyl, or a radical of formula -Alk-$OR^{13}$ or -Alk-$NR^{14}R^{15}$;
$R^{11}$ s hydrogen, $C_{1-6}$alkyl, $Ar^1$ or $Ar^1C_{1-6}$alkyl;
$R^{12}$ is hydrogen, $C_{1-6}$alkyl, $C_{1-6}$alkylcarbonyl, $C_{1-6}$alkyloxycarbonyl, $C_{1-6}$alkylaminocarbonyl, $Ar^1$, $Ar^1C_{1-6}$alkyl, $C_{1-6}$alkylcarbonyl-$C_{1-6}$alkyl, $Ar^1$carbonyl, $Ar^1C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino $C_{1-6}$alkylcarbonyl, amino, $C_{1-6}$alkylamino, $C_{1-6}$alkylcarbonylamino, or a radical of formula -Alk-$OR^{13}$ or -Alk-$NR^{14}R^{15}$;
wherein
Alk is $C_{1-6}$alkanediyl;
$R^{13}$ is hydrogen, $C_{1-6}$alkyl, $C_{1-6}$alkylcarbonyl, hydroxy-$C_{1-6}$alkyl, $Ar^1$ or $Ar^1C_{1-6}$alkyl;
$R^{14}$ is hydrogen, $C_{1-6}$alkyl, $Ar^1$ or $Ar^1C_{1-6}$alkyl;
$R^{15}$ is hydrogen, $C_{1-6}$alkyl, $C_{1-6}$alkylcarbonyl, $Ar^1$ or $Ar^1C_{1-6}$alkyl;
$R^6$ is a radical of formula

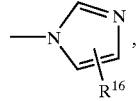

(b-1)

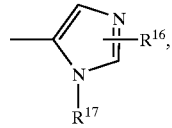

(b-2)

wherein $R^{16}$ is hydrogen, halo, $Ar^1$, $C_{1-6}$alkyl, hydroxy$C_{1-6}$alkyl, $C_{1-6}$alkyloxy-$C_{1-6}$alkyl, $C_{1-6}$alkyloxy, $C_{1-6}$alkylthio, amino, $C_{1-6}$alkyloxycarbonyl, $C_{1-6}$alkylthio$C_{1-6}$alkyl, $C_{1-6}$alkylS(O)$C_{1-6}$alkyl or $C_{1-6}$alkyl-S(O)$_2C_{1-6}$alkyl;
$R^{17}$ is hydrogen, $C_{1-6}$alkyl or di($C_{1-4}$alkyl) aminosulfonyl;
$R^7$ is hydrogen or $C_{1-6}$alkyl provided that the dotted line does not represent a bond;
$R^8$ is hydrogen, $C_{1-6}$alkyl or $Ar^2CH_2$ or $Het^1CH_2$;
$R^9$ is hydrogen, $C_{1-6}$alkyl, $C_{1-6}$alkyloxy or halo; or
$R^8$ and $R^9$ taken together to form a bivalent radical of formula —CH=CH— (c-1),
—$CH_2$—$CH_2$— (c-2),
—$CH_2$—$CH_2$—$CH_2$— (c-3),
—$CH_2$—O— (c-4), or —$CH_2$—$CH_2$—O— (c-5);

$Ar^1$ is phenyl; or phenyl substituted with 1 or 2 substituents each independently selected from halo, $C_{1-6}$alkyl, $C_{1-6}$alkyloxy or trifluoromethyl;
$Ar^2$ is phenyl; or phenyl substituted with 1 or 2 substituents each independently selected from halo, $C_{1-6}$alkyl, $C_{1-6}$alkyloxy or trifluoromethyl; and
$Het^1$ is pyridinyl; pyridinyl substituted with 1 or 2 substituents each independently selected from halo, $C_{1-6}$alkyl, $C_{1-6}$alkyloxy or trifluoromethyl.

Other useful farnesyl protein transferase inhibitors have the structure

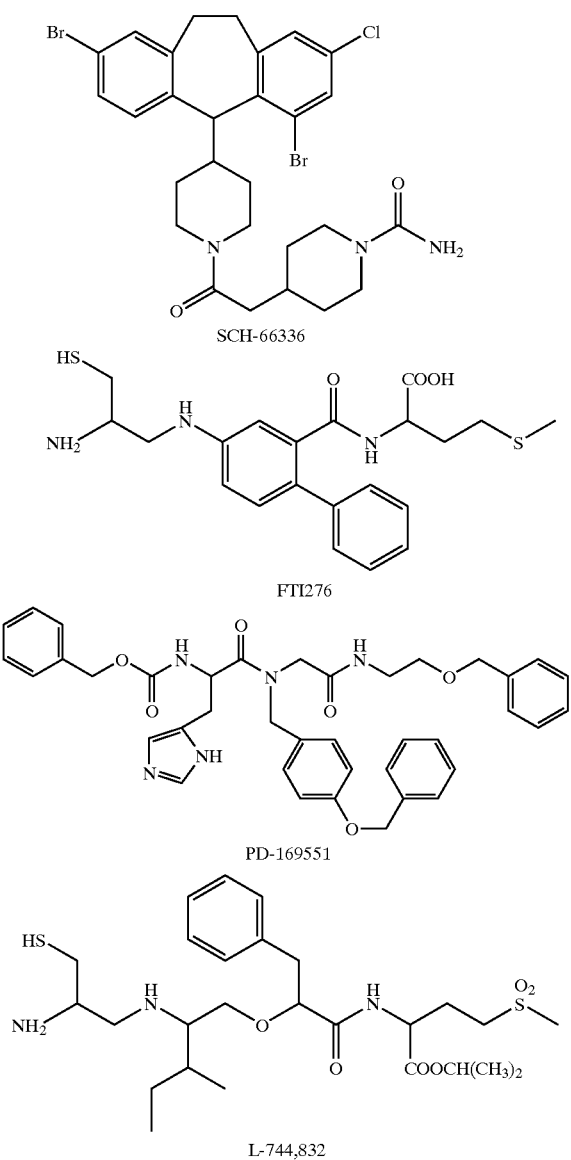

SCH-66336

FTI276

PD-169551

L-744,832

These farnesyl protein transferase inhibitors decrease the growth of tumors in vivo by a direct effect on tumor cell growth but also indirectly, i.e. by inhibiting angiogenesis (Rak. J. et al., Cancer Research, 55, 4575–4580, 1995). Consequently, treatment with these inhibitors suppresses solid tumor growth in vivo at least in part by inhibiting angiogenesis.

Unexpectedly, we have now found that farnesyl protein transferase inhibitors show in vivo activity against arthritis ; the beneficial effect can be attributed both to a decrease in the severity of the disease, as well as in the incidence.

Arthritis, in particular rheumatoid arthritis, is one of several joint diseases collectively known as arthropathies. The diseases are characterized by hyperproliferation of the synovial membrane in the joint, the formation of pannus, and the destruction of cartilage and bone. Arthropathies comprise rheumatoid arthritis, osteoarthritis, juvenile arthritis, polyarthritis, gout, epidemic polyarthritis (Ross River Virus infection), psoriatic arthritis, ankylosing spondylitis, systemic lupus erythematosus ; arthropathies can also be observed in Felty's syndrome, Reiter's syndrome and Still's syndrome.

Current therapy of arthropathies includes drugs such as steroids (e.g. prednisone), disease-modifying antirheumatic drugs (e.g. gold sodium thiomalate, methotrexate, hydroxychloroquine, sulfasalazine) and nonsteroidal antiinflammatory drugs; bed rest, splinting of the affected joints, application of local heat to the joint and physical therapy.

The present invention is concerned with the use of at least a farnesyl protein transferase inhibitor for the preparation of a pharmaceutical composition for treating arthropathies.

In particular, the present invention is concerned with the use of at least a farnesyl protein transferase inhibitor for the preparation of a pharmaceutical composition for treating arthropathies, wherein said farnesyl protein transferase inhibitor is an (imidazoly-5-yl)methyl-2-quinolinone derivative of formula (I), or a compound of formula (II) or (IfI) which is metabolized in vivo to the compound of formula (I), said compounds being represented by

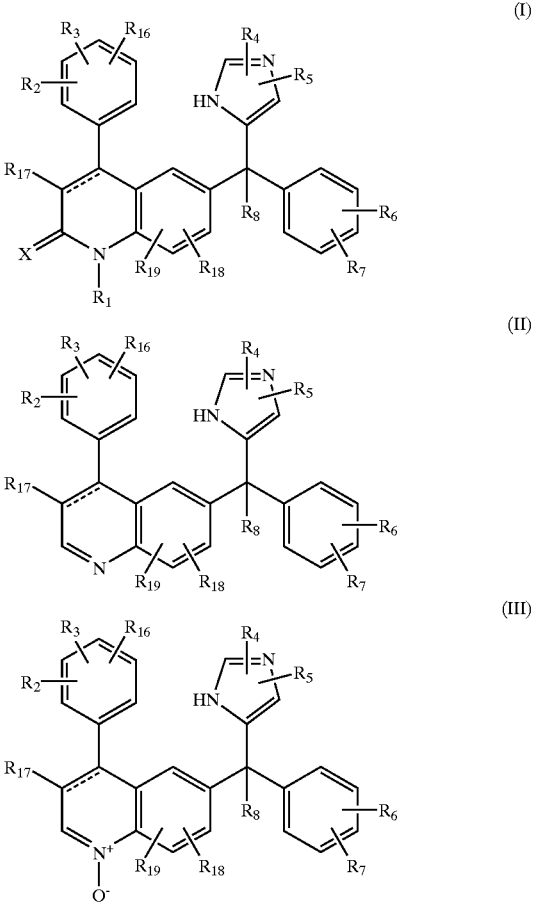

the pharmaceutically acceptable acid or base addition salts and the stereochemically isomeric forms thereof, wherein
the dotted line represents an optional bond;
X is oxygen or sulfur;
$R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl, or a radical of formula -Alk$^1$-C(=O)—R$^9$, -Alk$^1$-S(O)—R$^9$ or -Alk$^1$-S(O)$_2$—R$^9$,
wherein Alk$^1$ is $C_{1-6}$alkanediyl,
R$^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;

$R^2$, $R^3$ and $R^{16}$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino$C_{1-6}$alkyl-oxy, mono- or di($C_{1-6}$alkyl)amino$C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl, 4,4-dimethyloxazolyl; or when on adjacent positions $R^2$ and $R^3$ taken together may form a bivalent radical of formula —O—CH$_2$—O—  (a-1), —O—CH$_2$—CH$_2$—O—  (a-2), —O—CH=CH—  (a-3), —O—CH$_2$—CH$_2$—  (a-4), —O—CH$_2$—CH$_2$—CH$_2$—  (a-5), or —CH=CH—CH=CH—  (a-6);

$R^4$ and $R^5$ each independently are hydrogen, halo, $Ar^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2C_{1-6}$alkyl;

$R^6$ and $R^7$ each independently are hydrogen, halo, cyano, $C_{1-6}$alkyl, $C_{1-6}$alkyloxy, $Ar^2$oxy, trihalomethyl, $C_{1-6}$alkylthio, di($C_{1-6}$alkyl)amino, or when on adjacent positions $R^6$ and $R^7$ taken together may form a bivalent radical of formula —O—CH$_2$—O—  (c-1), or —CH=CH—CH=CH—  (c-2);

$R^8$ is hydrogen, $C_{1-6}$alkyl, cyano, hydroxycarbonyl, $C_{1-6}$alkyloxycarbonyl, $C_{1-6}$alkyl-carbonyl$C_{1-6}$alkyl, cyano$C_{1-6}$alkyl, $C_{1-6}$alkyloxycarbonyl$C_{1-6}$alkyl, carboxy-$C_{1-6}$alkyl, hydroxy$C_{1-6}$alkyl, amino$C_{1-6}$alkyl, mono- or di($C_{1-6}$alkyl)amino-$C_{1-6}$alkyl, imidazolyl, halo$C_{1-6}$alkyl, $C_{1-6}$alkyloxy$C_{1-6}$alkyl, aminocarbonyl-$C_{1-6}$alkyl, or a radical of formula —O—$R^{10}$  (b-1), —S—$R^{10}$  (b-2), —N—$R^{11}R^{12}$  (b-3), wherein
$R^{10}$ is hydrogen, $C_{1-6}$alkyl, $C_{1-6}$alkylcarbonyl, $Ar^1$, $Ar^2C_{1-6}$alkyl, $C_{1-6}$alkyloxycarbonyl$C_{1-6}$alkyl, or a radical or formula -Alk$^2$—OR$^{13}$ or -Alk$^2$-NR$^{14}R^{15}$;
$R^{11}$ is hydrogen, $C_{1-12}$alkyl, $Ar^1$ or $Ar^2C_{1-6}$alkyl;
$R^{12}$ is hydrogen, $C_{1-6}$alkyl, $C_{1-6}$alkylcarbonyl, $C_{1-6}$alkyloxycarbonyl, $C_{1-6}$alkylaminocarbonyl, $Ar^1$, $Ar^2C_{1-6}$alkyl, $C_{1-6}$-alkylcarbonyl-$C_{1-6}$alkyl, a natural amino acid, $Ar^1$carbonyl, $Ar^2C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical or formula -Alk$^2$-OR$^{13}$ or -Alk$^2$-NR$^{14}R^{15}$;
wherein
Alk$^2$ is $C_{1-6}$alkanediyl;
$R^{13}$ is hydrogen, $C_{1-6}$alkyl, $C_{1-6}$alkylcarbonyl, hydroxy-$C_{1-4}$alkyl, $Ar^1$ or $Ar^2C_{1-6}$alkyl;
$R^{14}$ is hydrogen, $C_{1-6}$alkyl, $Ar^1$ or $Ar^2C_{1-6}$alkyl;
$R^{15}$ is hydrogen, $C_{1-6}$alkyl, $C_{1-6}$alkylcarbonyl, $Ar^1$ or $Ar^2C_{1-6}$alkyl;
$R^{17}$ is hydrogen, halo, cyano, $C_{1-6}$alkyl, $C_{1-6}$alkyloxycarbonyl, $Ar^1$;
$R^{18}$ is hydrogen, $C_{1-6}$alkyl, $C_{1-6}$alkyloxy or halo;
$R^{19}$ is hydrogen or $C_{1-6}$alkyl;
$Ar^1$ is phenyl or phenyl substituted with $C_{1-6}$alkyl, hydroxy, amino, $C_{1-6}$alkyloxy or halo; and
$Ar^2$ is phenyl or phenyl substituted with $C_{1-6}$alkyl, hydroxy, amino, $C_{1-6}$alkyloxy or halo.

In Formulas (I), (II) and (III), $R^4$ or $R^5$ may also be bound to one of the nitrogen atoms in the imidazole ring. In that case the hydrogen on the nitrogen is replaced by $R^4$ or $R^5$ and the meaning of $R^4$ and $R^5$ when bound to the nitrogen is limited to hydrogen, $Ar^1$, $C_{1-6}$alkyl, hydroxy$C_{1-6}$alkyl, $C_{1-6}$alkyloxy$C_{1-6}$alkyl, $C_{1-6}$alkyloxycarbonyl, $C_{1-6}$alkylS(O)$C_{1-6}$alkyl, $C_{1-6}$alkylS(O)$_2C_{1-6}$alkyl.

As used in the foregoing definitions and hereinafter halo defines fluoro, chloro, bromo and iodo; $C_{1-6}$alkyl defines straight and branched chained saturated hydrocarbon radicals having from 1 to 6 carbon atoms such as, for example, methyl, ethyl, propyl, butyl, pentyl, hexyl and the like; $C_{1-8}$alkyl encompasses the straight and branched chained saturated hydrocarbon radicals as defined in $C_{1-6}$alkyl as well as the higher homologues thereof containing 7 or 8 carbon atoms such as, for example heptyl or octyl; $C_{1-12}$alkyl again encompasses $C_{1-8}$alkyl and the higher homologues thereof containing 9 to 12 carbon atoms, such as, for example, nonyl, decyl, undecyl, dodecyl; $C_{1-16}$alkyl again encompasses $C_{1-12}$alkyl and the higher homologues thereof containing 13 to 16 carbon atoms, such as, for example, tridecyl, tetradecyl, pentedecyl and hexadecyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof. The term "C(=O)" refers to a carbonyl group, "S(O)" refers to a sulfoxide and "S(O)$_2$" to a sulfon. The term "natural amino acid" refers to a natural amino acid that is bound via a covalent amide linkage formed by loss of a molecule of water between the carboxyl group of the amino acid and the amino group of the remainder of the molecule. Examples of natural amino acids are glycine, alanine, valine, leucine, isoleucine, methionine, proline, phenylanaline, tryptophan, serine, threonine, cysteine, tyrosine, asparagine, glutamine, aspartic acid, glutamic acid, lysine, arginine, histidine.

The pharmaceutically acceptable acid or base addition salts as mentioned hereinabove are meant to comprise the therapeutically active non-toxic acid and non-toxic base addition salt forms which the compounds of formulas (I), (II) and (III) are able to form. The compounds of formulas (I), (II) and (III) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formulas (I), (II) and (III) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formulas (I), (II) and (III) are able to form. Examples of such forms are e.g. hydrates, alcoholates and the like.

The term stereochemically isomeric forms of compounds of formulas (I), (II) and (III), as used hereinbefore, defines all possible compounds made up of the same atoms bonded by the same sequence of bonds but having different three-dimensional structures which are not interchangeable, which the compounds of formulas (I), (II) and (III) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formulas (I), (II) and (III) both in pure form or in admixture with each other are intended to be embraced within the scope of the present invention.

Some of the compounds of formulas (I), (II) and (III) may also exist in their tautomeric forms. Such forms although not explicitly indicated in the above formula are intended to be included within the scope of the present invention.

Whenever used hereinafter, the term "compounds of formulas (I), (II) and (III)" is meant to include also the pharmaceutically acceptable acid or base addition salts and all stereoisomeric forms.

Preferably the substituent $R^{18}$ is situated on the 5 or 7 position of the quinolinone moiety and substituent $R^{19}$ is situated on the 8 position when $R^{18}$ is on the 7-position.

Interesting compounds are these compounds of formula (I) wherein X is oxygen.

Also interesting compounds are these compounds of formula (I) wherein the dotted line represents a bond, so as to form a double bond.

Another group of interesting compounds are those compounds of formula (I) wherein $R^1$ is hydrogen, $C_{1-6}$alkyl, $C_{1-6}$alkyloxy$C_{1-6}$alkyl, di($C_{1-6}$alkyl)amino$C_{1-6}$alkyl, or a radical of formula-Alk$^1$-C(=O)—R$^9$, wherein Alk$^1$ is methylene and $R^9$ is $C_{1-8}$alkyl-amino substituted with $C_{1-6}$alkyloxycarbonyl.

Still another group of interesting compounds are those compounds of formula (I) wherein $R^3$ is hydrogen or halo; and $R^2$ is halo, $C_{1-6}$alkyl, $C_{2-6}$alkenyl, $C_{1-6}$alkyloxy, trihalomethoxy or hydroxy$C_{1-6}$alkyloxy.

A further group of interesting compounds are those compounds of formula (I) wherein $R^2$ and $R^3$ are on adjacent positions and taken together to form a bivalent radical of formula (a-1), (a-2) or (a-3).

A still further group of interesting compounds are those compounds of formula (I) wherein $R^5$ is hydrogen and $R^4$ is hydrogen or $C_{1-6}$alkyl.

Yet another group of interesting compounds are those compounds of formula (I) wherein $R^7$ is hydrogen; and $R^6$ is $C_{1-6}$alkyl or halo, preferably chloro, especially 4-chloro.

A particular group of compounds are those compounds of formula (I) wherein $R^8$ is hydrogen, hydroxy, halo$C_{1-6}$alkyl, hydroxy$C_{1-6}$alkyl, cyano$C_{1-6}$alkyl, $C_{1-6}$alkyloxy-carbonyl$C_{1-6}$alkyl, imidazolyl, or a radical of formula —NR$^{11}$R$^{12}$ wherein R$^{11}$ is hydrogen or $C_{1-12}$alkyl and R$^{12}$ is hydrogen, $C_{1-6}$alkyl, $C_{1-6}$alkyloxy, hydroxy, $C_{1-6}$alkyloxy$C_{1-6}$alkylcarbonyl, or a radical of formula -Alk$^2$-OR$^{13}$ wherein R$^{13}$ is hydrogen or $C_{1-6}$alkyl.

Preferred compounds are those compounds wherein R$^1$ is hydrogen, $C_{1-6}$alkyl, $C_{1-6}$alkyloxy$C_{1-6}$alkyl, di($C_{1-6}$alkyl) amino$C_{1-6}$alkyl, or a radical of formula -Alk$^1$-C(=O)—R$^9$, wherein Alk$^1$ is methylene and R$^9$ is $C_{1-8}$alkylamino substituted with $C_{1-6}$alkyloxycarbonyl; R$^2$ is halo, $C_{1-6}$alkyl, $C_{2-6}$alkenyl, $C_{1-6}$alkyloxy, trihalo-methoxy, hydroxy$C_{1-6}$alkyloxy or Ar$^1$; R$^3$ is hydrogen; R$^4$ is methyl bound to the nitrogen in 3-position of the imidazole; R$^5$ is hydrogen; R$^6$ is chloro; R$^7$ is hydrogen; R$^8$ is hydrogen, hydroxy, halo$C_{1-6}$alkyl, hydroxy$C_{1-6}$alkyl, cyano$C_{1-6}$alkyl, $C_{1-6}$alkyl-oxycarbonyl$C_{1-6}$alkyl, imidazolyl, or a radical of formula —NR$^{11}$R$^{12}$ wherein R$^{11}$ is hydrogen or $C_{1-12}$alkyl and R$^{12}$ is hydrogen, $C_{1-6}$alkyl, $C_{1-6}$alkyloxy, $C_{1-6}$alkyloxy $C_{1-6}$alkylcarbonyl, or a radical of formula -Alk$^2$-OR$^{13}$ wherein R$^{13}$ is $C_{1-6}$alkyl; R$^{17}$ is hydrogen and R$^{18}$ is hydrogen.

Most preferred compounds are
4-(3-chlorophenyl)-6-[(4-chlorophenyl)hydroxy(1-methyl-1H-imidazol-5-yl)methyl]-1-methyl-2(1H)-quinolinone,
6-[amino(4-chlorophenyl)-1-methyl-1H-imidazol-5-ylmethyl]-4-(3-chlorophenyl)-1-methyl-2(1H)-quinolinone;
6-[(4-chlorophenyl)hydroxy(1-methyl-1H-imidazol-5-yl) methyl]-4-(3-ethoxyphenyl)-1-methyl-2(1H)-quinolinone;
6-[(4-chlorophenyl)(1-methyl-1H-imidazol-5-yl)methyl]-4-(3-ethoxyphenyl)-1-methyl-2(1H)-quinolinone monohydrochloride.monohydrate;
6-[amino(4-chlorophenyl)(1-methyl-1H-imidazol-5-yl) methyl]-4-(3-ethoxyphenyl)-1-methyl-2(1H)-quinolinone,
6-amino(4-chlorophenyl)(1-methyl-1H-imidazol-5-yl) methyl]-1-methyl-4-(3-propylphenyl)-2(1H)-quinolinone; a stereoisomeric form thereof or a pharmaceutically acceptable acid or base addition salt; and
(+)-6-[amino(4-chlorophenyl)(1-methyl-1H-imidazol-5-yl) methyl]-4-(3-chlorophenyl)-1-methyl-2(1H)-quinolinone (Compound 75 in Table 1 of the Experimental part); or a pharmaceutically acceptable acid addition salt thereof.

Farnesyl protein transferase inhibitors can be formulated into pharmaceutical compositions as known in the art; for the compounds of formulas (I), (II) and (III) suitable examples can be found in WO-97/21701. To prepare the aforementioned pharmaceutical compositions, a therapeutically effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous, or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellent such as nitrogen, carbon dioxide, a freon, or without a propellent such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Preferably, a therapeutically effective amount of the pharmaceutical composition comprising a farnesyl protein transferase inhibitor is administered orally or parenterally. Said therapeutically effective amount is the amount that effectively decreases the severity of arthritis, i.e. dimishes the swelling and the tenderness of the joints and reduces the pain, or the amount that reduces the incidence, i.e. the number of swollen and tender joints. On the basis of the current data, it appears that a pharmaceutical composition comprising (+)-6-[amino(4-chlorophenyl) (1-methyl-1H-imidazol-5-yl)methyl]-4-(3-chlorophenyl)-1-methyl-2(1H)-quinolinone (compound 75) as the active ingredient can be administered orally in an amount of from 10 to 1500 mg daily, either as a single dose or subdivided into more than one dose. A preferred amount ranges from 100 to 1,000 mg daily.

The therapy of arthropathies using farnesyl protein transferase inhibitors can conveniently be combined with drug therapies using steroids (e.g. prednisone), disease-modifying antirheumatic drugs (e.g. gold sodium thiomalate, methotrexate, hydroxychloroquine, sulfasalazine) and nonsteroidal antiinflammatory drugs; bed rest, splinting of the affected joints, application of local heat to the joint and physical therapy.

The present invention also concerns a method of treating arthropathies in a mammal comprising the step of administering a therapeutically effective amount of a farnesyl protein tranferase inhibitor to said mammal.

Experimental Part

The following tables show the formulas of the compounds of formula (I), their physical data, and references to the examples in WO-97/21701 according to which the compounds in question may be prepared. In the pharmacological example, the effect of the compounds of formula (I) on induced arthritis is illustrated.

TABLE 1

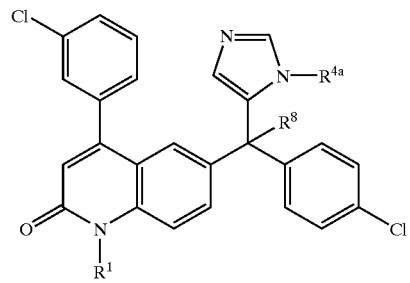

| Co. No. | Ex. No. | $R^1$ | $R^{4a}$ | $R^8$ | Physical data |
|---|---|---|---|---|---|
| 3 | B.1 | $CH_3$ | $CH_3$ | OH | mp. 233.6° C. |
| 4 | B.3 | $CH_3$ | $CH_3$ | $OCH_3$ | mp. 140–160° C.; .$C_2H_2O_4.H_2O$ |

TABLE 1-continued

| Co. No. | Ex. No. | R$^1$ | R$^{4a}$ | R$^8$ | Physical data |
|---|---|---|---|---|---|
| 5 | B.6 | CH$_3$ | CH$_3$ | H | mp. 165° C.; .C$_2$H$_2$O$_4$.H$_2$O |
| 6 | B.5 | CH$_3$ | CH$_2$CH$_3$ | H | mp. 180° C.; .C$_2$H$_2$O$_4$.1/2H$_2$O |
| 7 | B.2 | H | CH$_3$ | H | mp. 260° C. |
| 8 | B.2 | H | (CH$_2$)$_3$CH$_3$ | OH | — |
| 9 | B.4 | CH$_3$ | (CH$_2$)$_3$CH$_3$ | OH | mp. 174° C. |
| 10 | B.3 | H | CH$_3$ | OCH$_2$COOCH$_2$CH$_3$ | mp. 185° C.; .3/2C$_2$H$_2$O$_4$ |
| 11 | B.3 | CH$_3$ | CH$_3$ | O(CH$_2$)$_2$N(CH$_3$)$_2$ | mp. 120° C. |
| 12 | B.7 | CH$_3$ | CH$_3$ | CH$_3$ | mp. 210° C.; .C$_2$H$_2$O$_4$ |
| 13 | B.7 | CH$_3$ | CH$_3$ | CH$_2$CH$_3$ | mp. 196° C.; .C$_2$H$_2$O$_4$ |
| 14 | B.13 | CH$_3$ | CH$_3$ | NH$_2$ | mp. 220° C. |
| 72 | B.13 | CH$_3$ | CH$_3$ | NH$_2$ | .3/2-(E)—C$_4$H$_4$O$_4$ |
| 73 | B.13 | CH$_3$ | CH$_3$ | NH$_2$ | .2HCl |
| 74 | B.8b | CH$_3$ | CH$_3$ | NH$_2$ | (A) |
| 75 | B.8b | CH$_3$ | CH$_3$ | NH$_2$ | (+) |
| 15 | B.3 | CH$_3$ | CH$_3$ | O(CH$_2$)$_3$OH | mp. 135° C. |
| 16 | B.3 | CH$_3$ | CH$_3$ | O(CH$_2$)$_2$CH$_3$ | mp. 180° C.; .C$_2$H$_2$O$_4$.3/2(H$_2$O) |
| 17 | B.3 | CH$_3$ | CH$_3$ | O(CH$_2$)$_2$O—C$_6$H$_5$ | mp. 144° C.; .3/2(C$_2$H$_2$O$_4$) |
| 18 | B.2 | H | CH(CH$_3$)$_2$ | OH | — |
| 19 | B.4 | CH$_3$ | CH(CH$_3$)$_2$ | OH | mp. 254° C. |
| 20 | B.2 | H | (CH$_2$)$_2$OCH$_3$ | OH | mp. 112° C. |
| 21 | B.4 | CH$_3$ | (CH$_2$)$_2$OCH$_3$ | OH | mp. 192° C. |
| 22 | B.3 | CH$_3$ | CH$_3$ | O(CH$_2$)$_2$OH | mp. 198° C. |
| 23 | B.8a | CH$_3$ | CH$_3$ | OH | mp. 150–200° C.; (A); .C$_2$H$_2$O$_4$ |
| 24 | B.8a | CH$_3$ | CH$_3$ | OH | mp. 150–200° C.; (B); .C$_2$H$_2$O$_4$ |
| 25 | B.11 | CH$_3$ | CH$_3$ | CH$_2$—CN | mp. 154° C. |
| 27 | B.2 | H | (CH$_2$)$_3$OCH$_3$ | OH | — |
| 28 | B.4 | CH$_3$ | (CH$_2$)$_3$OCH$_3$ | OH | mp. 196° C.; .H$_2$O |
| 29 | B.3 | CH$_3$ | CH$_3$ | O(CH$_2$)$_3$OCH$_2$CH$_3$ | mp. 105° C.; .3/2(H$_2$O) |
| 31 | B.2 | H | CH$_3$ | OH | >260° C. |
| 32 | B.6 | CH$_3$ | (CH$_2$)$_2$OCH$_3$ | H | mp. 140° C.; .3/2(C$_2$H$_2$O$_4$) |
| 33 | B.6 | CH$_3$ | (CH$_2$)$_3$OCH$_3$ | H | mp. 180° C.; .HCl |
| 56 | B.12 | CH$_3$ | CH$_3$ | —NHCOCH$_3$ | .C$_2$H$_2$O$_4$ |
| 58 | B.11 | CH$_3$ | CH$_3$ | —CH$_2$COOCH$_2$CH$_3$ | .C$_2$H$_2$O$_4$.3/2(H$_2$O) |
| 60 | B.11 | CH$_3$ | CH$_3$ | 1-imidazolyl | — |
| 61 | B.21 | CH$_3$ | CH$_3$ | —NH—CH$_3$ | mp. 164° C. |
| 65 | B.2 | H | (CH$_2$)$_3$SOCH$_3$ | OH | .H$_2$O |
| 66 | B.13 | CH$_3$ | CH$_3$ | —N(CH$_3$)$_2$ | .2C$_2$H$_2$O$_4$.H$_2$O mp. 160° C. |
| 67 | B.13 | CH$_3$ | CH$_3$ | —NH—(CH$_2$)$_2$OCH$_3$ | mp. 216° C. |
| 68 | B.13 | CH$_3$ | CH$_3$ | —NH—(CH$_2$)$_2$—OH | — |
| 69 | B.7 | CH$_3$ | CH$_3$ | —CH$_2$Cl | .2C$_2$H$_2$O$_4$ mp. 220° C. |
| 70 | B.7 | CH$_3$ | CH$_3$ | —CH$_2$Br | — |
| 71 | * | CH$_3$ | CH$_3$ | —CH$_2$OH | .2C$_2$H$_2$O$_4$ |
| 76 | B.4 | —(CH$_2$)$_2$OCH$_3$ | CH$_3$ | OH | mp. 150° C. |
| 77 | * | CH$_3$ | CH$_3$ | —CH$_2$OCH$_3$ | .2C$_2$H$_2$O$_4$ mp. 166° C. |
| 78 | B.13 | CH$_3$ | CH$_3$ | —NH—OCH$_3$ | mp. 170° C. |
| 79 | B.20 | CH$_3$ | CH$_3$ | —NH—CONH$_2$ | .2H$_2$O |
| 80 | ** | CH$_3$ | CH$_3$ | —CH$_2$CONH$_2$ | — |

TABLE 1-continued

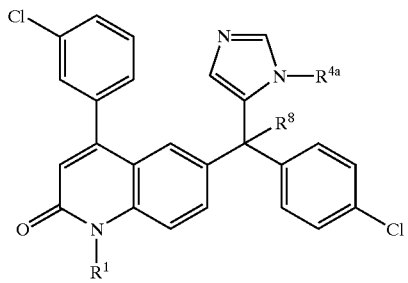

| Co. No. | Ex. No. | R$^1$ | R$^{4a}$ | R$^8$ | Physical data |
|---|---|---|---|---|---|
| 81 | B.13 | CH$_3$ | CH$_3$ | —NH—OH | — |
| 82 | B.13 | CH$_3$ | CH$_3$ | —NH(CH$_2$)$_2$N(CH$_3$)$_2$ | — |
| 83 | B.4 | (CH$_2$)$_2$N(CH$_3$)$_2$ | CH$_3$ | OH | .3/2C$_2$H$_2$O$_4$ .3/2H$_2$O mp. 200° C. |
| 84 | * | CH$_3$ | CH$_3$ | —CH$_2$N(CH$_3$)$_2$ | .C$_2$H$_2$O$_4$ mp. 210° C. |
| 85 | B.4 | CH$_3$ | CH$_3$ | —N(CH$_3$)$_2$ | — |
| 86 | B.4 | CH$_3$ | CH$_3$ | NHCOCH$_2$N(CH$_3$)$_2$ | — |
| 87 | B.4 | CH$_3$ | CH$_3$ | —NH(CH$_2$)$_9$CH$_3$ | — |
| 88 | B.4 | CH$_3$ | CH$_3$ | —NH(CH$_2$)$_2$NH$_2$ | — |
| 89 | B.20 | CH$_3$ | CH$_3$ | —NHCOCH$_2$OCH$_3$ | .HCl mp. 220° C. |
| 90 | B.6 | CH$_3$ | CH$_3$ | H | — |
| 91 | B.20 | CH$_3$ | CH$_3$ | —NHCOCH$_2$C$_6$H$_5$ | .C$_2$H$_2$O$_4$.H$_2$O mp. 170° C. |
| 92 | B.20 | CH$_3$ | CH$_3$ | —NHCOC$_6$H$_5$ | mp. 242° C. |
| 93 | B.20 | CH$_3$ | CH$_3$ | —NHCOCONH$_2$ | .C$_2$H$_2$O$_4$.H$_2$O mp. 186° C. |
| 94 | B.13 | CH$_3$ | CH$_3$ | —NHC$_6$H$_5$ | mp. 165° C. |

*prepared by functional-group transformation of compound 70
**prepared by functional-group transformation of compound 25

TABLE 2

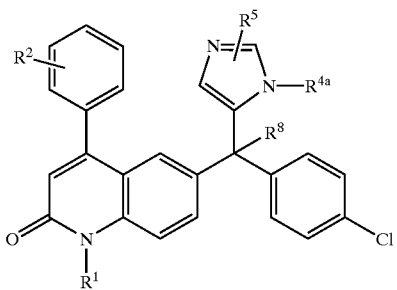

| Co. No. | Ex. No. | R$^1$ | R$^2$ | R$^{4a}$ | R$^5$ | R$^8$ | Physical data |
|---|---|---|---|---|---|---|---|
| 1 | B.1 | CH$_3$ | H | CH$_3$ | H | OH | mp. >250° C. |
| 2 | B.5 | CH$_3$ | H | CH$_3$ | H | H | mp. 100–110° C. |
| 26 | B.1 | CH$_3$ | 3-Cl | CH$_3$ | 2-CH$_3$ | OH | mp. 200° C. |
| 30 | B.6 | CH$_3$ | 3-Cl | CH$_3$ | 2-CH$_3$ | H | mp. 120–140° C.; .3/2(C$_2$H$_2$O$_4$).H$_2$O |
| 34 | B.1 | CH$_3$ | 3-O—CH$_2$—CH$_3$ | CH$_3$ | H | OH | mp. 190° C. |
| 35 | B.6 | CH$_3$ | 3-O—CH$_2$—CH$_3$ | CH$_3$ | H | H | mp. 160–180° C.; .HCl.H$_2$O |
| 36 | B.1 | CH$_3$ | 3-O—CH$_3$ | CH$_3$ | H | OH | mp. 210° C. |
| 37 | B.1 | CH$_3$ | 3-O—(CH$_2$)$_2$—CH$_3$ | CH$_3$ | H | OH | mp. 150–160° C. |
| 38 | B.1 | CH$_3$ | 3-O—(CH$_2$)$_3$—CH$_3$ | CH$_3$ | H | OH | mp. 150–160° C. |
| 49 | B.1 | CH$_3$ | 4-O—CH$_2$—CH$_3$ | CH$_3$ | H | OH | mp. 184.2° C. |
| 50 | B.1 | CH$_3$ | 3-O—CH—(CH$_3$)$_2$ | CH$_3$ | H | OH | mp. 147.1° C. |
| 51 | B.6 | CH$_3$ | 3-O—(CH$_2$)$_3$—CH$_3$ | CH$_3$ | H | H | mp. 164.2° C.; .3/2(C$_2$H$_2$O$_4$) |
| 52 | B.6 | CH$_3$ | 3-O—(CH$_2$)$_2$—CH$_3$ | CH$_3$ | H | H | .3/2(C$_2$H$_2$O$_4$) |
| 53 | B.6 | CH$_3$ | 3-O—CH—(CH$_3$)$_2$ | CH$_3$ | H | H | mp. 133.9° C.; .C$_2$H$_2$O$_4$.H$_2$O |

TABLE 2-continued

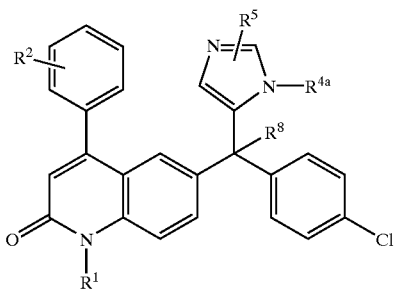

| Co. No. | Ex. No. | R¹ | R² | R⁴ᵃ | R⁵ | R⁸ | Physical data |
|---|---|---|---|---|---|---|---|
| 54 | B.14 | CH₃ | 3-OH | CH₃ | H | OH | — |
| 64 | B.10 | CH₃ | 3-OH | CH₃ | H | OH | .HCl.H₂O |
| 55 | B.6 | CH₃ | 3-OH | CH₃ | H | H | mp. >250° C. |
| 57 | B.1 | CH₃ | 2-OCH₂CH₃ | CH₃ | H | OH | — |
| 59 | B.13 | CH₃ | 3-OCH₂CH₃ | CH₃ | H | NH₂ | — |
| 95 | B.8a | CH₃ | 3-OCH₂CH₃ | CH₃ | H | NH₂ | (A) |
| 96 | B.8a | CH₃ | 3-OCH₂CH₃ | CH₃ | H | NH₂ | (B) |
| 62 | B.15 | CH₃ | 3-O(CH₂)₂N(CH₃)₂ | CH₃ | H | OH | — |
| 63 | B.11 | CH₃ | 3-O(CH₂)₂—OH | CH₃ | H | OH | — |
| 97 | B.1 | CH₃ | 3-CH₂CH₃ | CH₃ | H | OH | — |
| 98 | B.13 | CH₃ | 3-CH₂CH₃ | CH₃ | H | NH₂ | mp. 240° C. |
| 99 | B.1 | CH₃ | 3-(CH₂)₂CH₃ | CH₃ | H | OH | — |
| 100 | B.13 | CH₃ | 3-(CH₂)₂CH₃ | CH₃ | H | NH₂ | — |
| 101 | * | CH₃ | 3-O—(CH₂)₂OCH₃ | CH₃ | H | OH | .3/2(C₂—H₂O₄) mp. 193° C. |
| 102 | B.1 | CH₃ | 3-CH₃ | CH₃ | H | OH | mp. >250° C. |
| 103 | B.13 | CH₃ | 3-CH₃ | CH₃ | H | NH₂ | — |
| 104 | B.1 | CH₃ | 3-Br | CH₃ | H | OH | — |
| 105 | B.13 | CH₃ | 3-Br | CH₃ | H | NH₂ | — |
| 106 | B.1 | CH₃ | 3-O—CF₃ | CH₃ | H | OH | — |
| 107 | B.13 | CH₃ | 3-O—CF₃ | CH₃ | H | NH₂ | mp. 168° C. |
| 108 | B.1 | CH₃ | 3-C₆H₅ | CH₃ | H | OH | — |
| 109 | B.13 | CH₃ | 3-C₆H₅ | CH₃ | H | NH₂ | — |
| 110 | B.1 | CH₃ | 3-F | CH₃ | H | OH | — |
| 111 | B.13 | CH₃ | 3-F | CH₃ | H | NH₂ | mp. >250° C. |
| 112 | B.1 | CH₃ | 3-(E)—CH=CH—CH₃ | CH₃ | H | OH | mp. >250° C. |
| 113 | B.2 | H | 3-Cl | CH₃ | 3-Cl | OH | — |
| 114 | B.4 | CH₃ | 3-Cl | CH₃ | 3-Cl | OH | — |
| 115 | B.1 | CH₃ | 3-Cl | H | 3-CH₃ | OH | — |
| 116 | B.4 | CH₃ | 3-Cl | CH₃ | 3-CH₃ | OH | — |
| 117 | ** | CH₃ | 3-CN | CH₃ | H | OH | — |
| 160 | B.1 | CH₃ | 3-CF₃ | CH₃ | H | OH | — |

*prepared by functional-group transformation of compound 54
**prepared by functional-group transformation of compound 104

TABLE 3

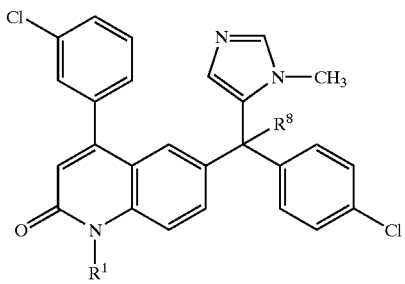

| Co. No. | Ex. No. | R¹ | R⁸ | Physical data |
|---|---|---|---|---|
| 39 | B.4 | CH₂CONHCH(COOCH₃)(CH₂CH(CH₃)₂) | H | mp. 240° C. (S) |
| 40 | B.4 | CH₂-2-quinolinyl | H | mp. 240° C.; .2 HCl |
| 41 | B.4 | CH₂CONHCH(COOCH₃)(CH₂CH(CH₃)₂) | OH | mp. >260° C. (S) |

TABLE 4

| Co. No. | Ex. No. | R² | R⁴ | R⁵ᵃ | R⁶ | R⁸ | Physical data |
|---|---|---|---|---|---|---|---|
| 42 | B.6 | H | H | H | 4-Cl | H | mp. 170° C.; .C₂H₂O₄ .1/2H₂O |
| 43 | B.10 | H | H | H | 4-Cl | OH | mp. 180° C.; .H₂O |
| 44 | B.5 | H | H | CH₃ | 4-Cl | H | mp. 152° C. |
| 45 | B.6 | 3-Cl | H | H | 4-Cl | H | mp. 175° C.; .C₂H₂O₄ |
| 46 | B.5 | 3-Cl | H | CH₂CH₃ | 4-Cl | H | mp. 132° C.; .C₂H₂O₄ |
| 47 | B.5 | 3-Cl | H | CH₃ | 4-Cl | H | mp. 115° C.; .3/2C₂H₂O₄ |
| 48 | B.9 | 3-Cl | H | CH₃ | 4-Cl | OH | mp. 230° C. |
| 118 | B.4 | 3-Cl | 3-CH₃ | CH₃ | 4-Cl | OH | mp. 222° C. |

TABLE 5

| Co. No. | Ex. No. | -R²-R³- | R⁶ | R⁸ |
|---|---|---|---|---|
| 119 | B.1 | —O—CH₂—O— | 4-Cl | OH |
| 120 | B.13 | —O—CH₂—O— | 4-Cl | NH₂ |
| 121 | B.1 | —O—CH₂—CH₂—O— | 4-Cl | OH |
| 122 | B.13 | —O—CH₂—CH₂—O— | 4-Cl | NH₂ |
| 123 | B.1 | —O—CH=CH— | 4-Cl | OH |

TABLE 6

| Co. No. | Ex. No. | X | R² | R³ | R¹⁶ | R⁸ | Physical data |
|---|---|---|---|---|---|---|---|
| 124 | B.1 | O | double | 3-OCH₃ | 4-OCH₃ | 5-OCH₃ | OH | mp. 230° C. |
| 125 | B.13 | O | double | 3-OCH₃ | 4-OCH₃ | 5-OCH₃ | NH₂ | mp. 218° C. |
| 126 | B.1 | O | single | 3-Cl | H | H | OH | .C₂H₂O₄ mp. 160° C. |
| 127 | B.1 | O | single | 3-Cl | H | H | OH | — |
| 128 | B.16 | S | double | 3-Cl | H | H | H | — |

TABLE 7

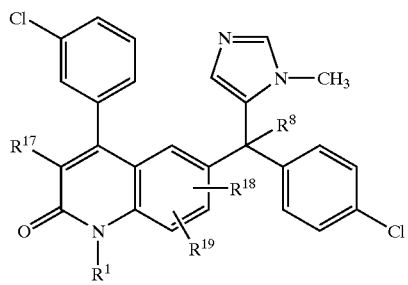

| Co. No. | Ex. No. | R¹ | R¹⁷ | R¹⁸ | R¹⁹ | R⁸ | Physical data |
|---|---|---|---|---|---|---|---|
| 129 | B.17 | H | CN | H | H | H | — |
| 130 | B.4 | CH₃ | CN | H | H | H | mp. 202° C. |
| 131 | B.17 | H | CN | H | H | OH | — |
| 132 | B.4 | CH₃ | CN | H | H | OH | — |
| 133 | B.17 | H | CN | H | H | —CH₂CN | — |
| 134 | B.4 | CH₃ | CN | H | H | —CH₂CN | mp. 138° C. |
| 135 | B.18 | H | CH₃ | H | H | OH | — |
| 136 | B.4 | CH₃ | CH₃ | H | H | OH | — |
| 137 | B.13 | CH₃ | CH₃ | H | H | NH₂ | mp. >250° C. |
| 138 | B.18 | H | C₆H₅ | H | H | H | — |
| 139 | B.4 | CH₃ | C₆H₅ | H | H | H | .3/2(C₂H₂O₄) mp. 180° C. |
| 140 | B.18 | H | C₆H₅ | H | H | OH | — |
| 141 | B.4 | CH₃ | C₆H₅ | H | H | OH | — |
| 142 | B.13 | CH₃ | C₆H₅ | H | H | NH₂ | — |
| 143 | B.13 | CH₃ | Cl | H | H | NH₂ | — |
| 144 | B.17 | H | —COOCH₂CH₃ | H | H | OH | — |
| 145 | B.4 | CH₃ | —COOCH₂CH₃ | H | H | OH | — |
| 146 | B.1 | CH₃ | H | 8-CH₃ | H | OH | — |
| 147 | B.13 | CH₃ | H | 8-CH₃ | H | NH₂ | .H₂O |
| 148 | B.1 | CH₃ | H | 7-Cl | H | OH | — |
| 149 | B.1 | CH₃ | H | 7-CH₃ | H | OH | — |
| 150 | B.1 | CH₃ | H | 5-CH₃ | H | OH | — |
| 151 | B.1 | CH₃ | H | 8-OCH₃ | H | OH | — |
| 161 | B.1 | CH₃ | H | 7-CH₃ | 8-CH₃ | OH | mp. 255° C. |

TABLE 8

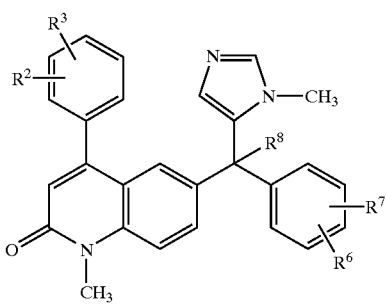

| Co. No. | Ex. No. | R² | R³ | R⁶ | R⁷ | R⁸ | Physical data |
|---|---|---|---|---|---|---|---|
| 152 | B.1 | 3-OCH₂CH₃ | H | 4-OCH₂CH₃ | H | OH | .3/2(C₂H₂O₄) |
| 153 | B.1 | 3-Cl | H | H | H | OH | — |
| 154 | B.1 | 3-Cl | H | 4-CH₃ | H | OH | — |
| 155 | B.1 | 3-Cl | H | 4-OCH₃ | H | OH | — |
| 156 | B.1 | 3-Cl | H | 4-CF₃ | H | OH | — |
| 157 | B.1 | 3-Cl | H | 2-Cl | 4-Cl | OH | — |
| 158 | B.1 | 3-Cl | 5-Cl | 4-Cl | H | OH | — |

TABLE 8-continued

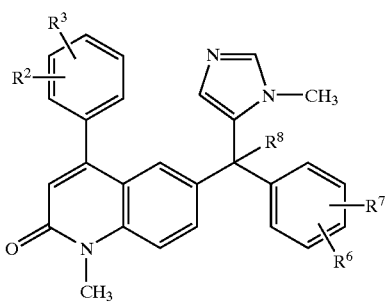

| Co. No. | Ex. No. | R² | R³ | R⁶ | R⁷ | R⁸ | Physical data |
|---|---|---|---|---|---|---|---|
| 159 | B.1 | (4,4-dimethyl-4,5-dihydrooxazol-2-yl) | H | 4-Cl | H | OH | — |
| 162 | B.1 | 3-Cl | H | 4-S—CH₃ | H | OH | mp. 169° C. .C₂H₂O₄.H₂O; |
| 163 | B.1 | 3-Cl | H | 4-N(CH₃)₂ | H | OH | mp. decomposes >172° C. |
| 164 | B.1 | 3-Cl | H | —CH=CH—CH=CH—* | | OH | .C₂H₂O₄ |

*R⁶ and R⁷ taken together to form a bivalent radical between positions 3 and 4 on the phenyl moiety

PHARMACOLOGICAL EXAMPLES

Example 1

Prophylactic Treatment

Male DBA1/J mice were immunized intradermally with collagen type II emulsified in complete Freund's Adjuvant on day 0 and day 21. Treatment of mice was started on day 20 (10 animals/treatment group). Mice were treated orally twice daily (6 hours time interval) with vehicle [DMSO: cremophor: 0.9% NaCl solution, 1:1:8 (v:v:v)] or compound 75 at a dose of 100 mg/kg. Three times per week symptoms of arthritis were scored. Animals were treated till day 36, at day 37 animals were sacrificed, blood was collected for analysis of anti-collagen antibodies, radiographs were made and paws were fixed for histological evaluation. The compound did not show any signs of toxicity and no lethalities were observed. Trained lab personnel evaluated the severity and incidence of the arthritic symptoms at regular intervals without knowing which animals had received vehicle or drug.

In Table 9, the mean arthritic score is shown. For each paw, a score ranging from 0 (normal) to 2 (maximal redness and swelling) is given. The score for the 4 paws is summed up and averaged for the 10 animals per group (=Mean arthritic score). Compound 75 clearly suppresses the arthritic score.

TABLE 9

| | Mean Arthritic Score | |
|---|---|---|
| Days after immunization | Vehicle (2 ×) | Compound 75– 100 mpk (2 ×) |
| 22 | 0.00 | 0.00 |
| 24 | 0.28 | 0.05 |
| 27 | 1.53 | 0.60 |
| 29 | 4.23 | 0.90 |
| 31 | 4.65 | 1.03 |
| 34 | 5.08 | 0.80 |
| 36 | 4.95 | 0.75 |
| 37 | 4.90 | 0.80 |

Table 10 hows the incidence of arthritis. In the vehicle group the incidence is 9 or 10 animals per group. The incidence for the group treated with Compound 75 is 7 or 8 animals out of 10.

TABLE 10

| | Incidence of arthritis (% of animals affected) | |
|---|---|---|
| Days after immunization | Vehicle (2 ×) | Compound 75– 100 mpk (2 ×) |
| 22 | 0 | 0 |
| 24 | 30 | 20 |
| 27 | 60 | 40 |
| 29 | 90 | 80 |
| 31 | 90 | 70 |
| 34 | 100 | 60 |
| 36 | 100 | 70 |
| 37 | 100 | 60 |

Table 11 summarizes the results of the observations for the occurrence of ankylosis as the arthritis progresses. Each paw is scored as follows: 0 for no ankylosis, 1 for ankylosis. Again the results for the four paws are summed up and averaged for the 10 animals. At the end of the experiment, the ankylosis score in the vehicle group (3.1) is clearly higher than that in the group treated with Compound 75 (1.2).

TABLE 11

Ankylosis score

| Days after immunization | Vehicle (2 ×) | Compound 75– 100 mpk (2 ×) |
|---|---|---|
| 22 | 0.00 | 0.00 |
| 24 | 0.00 | 0.00 |
| 27 | 0.70 | 0.30 |
| 29 | 2.20 | 0.80 |
| 31 | 2.30 | 1.10 |
| 34 | 2.90 | 1.20 |
| 36 | 3.70 | 1.40 |
| 37 | 3.10 | 1.20 |

In Table 12, the incidence of ankylosis is given. In the vehicle group the incidence is 90 to 100%, but only 60% in the group of animals treated with Compound 75.

TABLE 12

Incidence of ankylosis (% of animals affected)

| Days after immunization | Vehicle (2 ×) | Compound 75– 100 mpk (2 ×) |
|---|---|---|
| 22 | 0 | 0 |
| 24 | 0 | 0 |
| 27 | 50 | 10 |
| 29 | 80 | 50 |
| 31 | 90 | 50 |
| 34 | 100 | 50 |
| 36 | 100 | 60 |
| 37 | 100 | 60 |

In Table 13 the mean number of affected paws in the vehicle and compound treated test animals is shown; compound 75 reduces that number.

TABLE 13

Mean number of affected paws

| Days after immunization | Vehicle (2 ×) | Compound 75– 100 mpk (2 ×) |
|---|---|---|
| 22 | 0.00 | 0.00 |
| 24 | 0.40 | 0.20 |
| 27 | 1.60 | 0.80 |
| 29 | 2.80 | 1.30 |
| 31 | 2.80 | 1.70 |
| 34 | 3.30 | 1.20 |
| 36 | 3.20 | 1.30 |
| 37 | 3.20 | 1.30 |

In conclusion, oral administration twice daily of compound 75 to test animals wherein arthritis is induced by collagen type II, reduces the mean arthritic score; the beneficial effect is due to both a reduction of the severity (lower score per paw) and a reduction of the incidence (fewer paws affected).

Example 2

Therapeutic Treatment

Male DBA1/J mice were immunized intradernally with collagen type II emulsified in complete Freund's Adjuvant on day 0 and day 21. Treatment of mice was started on day 30 (10 animals/treatment group; the animals were randomized so that both groups had similar arthritic symptoms at the start). Mice were treated orally with vehicle [DMSO: cremophor: 0.9% NaCl solution, 1:1:8 (v:v:v)] or compound 75 at a dose of 100 mg/kg. Three times per week symptoms of arthritis were scored. Animals were treated till day 49, at day 50 animals were sacrificed, blood was collected for analysis of anti-collagen antibodies, and radiographs were. The compound did not show any signs of toxicity and no lethalities were observed.

Trained lab personnel evaluated the severity and incidence of the arthritic symptoms at regular intervals without knowing which animals had received vehicle or drug.

In Table 14, the mean arthritic score is shown. For each paw, a score ranging from 0 (normal) to 2 (maximal redness and swelling) is given. The score for the 4 paws is summed up and averaged for the 10 animals per group (=Mean arthritic score). Compound 75 clearly suppresses the arthritic score.

TABLE 14

Mean Arthritic Score

| Days after immunization | Vehicle | Compound 75– 100 mpk |
|---|---|---|
| 22 | 0.00 | 0.00 |
| 24 | 0.00 | 0.03 |
| 28 | 3.75 | 3.50 |
| 29 | 4.08 | 4.25 |
| 31 | 4.98 | 4.03 |
| 34 | 5.18 | 3.80 |
| 36 | 4.80 | 3.00 |
| 38 | 4.73 | 3.20 |
| 41 | 4.88 | 3.45 |
| 43 | 4.18 | 2.15 |
| 45 | 3.28 | 1.33 |
| 48 | 2.55 | 1.58 |
| 50 | 2.33 | 0.88 |

Table 15 shows the incidence of arthritic symptoms. The incidence is 100% at the start of treatment. At the end of the treatment period, the incidence in the vehicle group is reduced to 80%, while in the group treated with compound 75 the incidence is 60%.

TABLE 15

Incidence of arthritis (% of animals affected)

| Days after immunization | Vehicle | Compound 75– 100 mpk |
|---|---|---|
| 22 | 0 | 0 |
| 24 | 0 | 10 |
| 28 | 90 | 90 |
| 29 | 100 | 100 |
| 31 | 100 | 100 |
| 34 | 100 | 100 |
| 36 | 100 | 90 |
| 38 | 100 | 90 |
| 41 | 100 | 90 |
| 43 | 100 | 90 |
| 45 | 80 | 100 |
| 48 | 90 | 60 |
| 50 | 80 | 60 |

Table 16 summarizes the results of the observations for the occurrence of ankylosis as the arthritis progresses. Each paw is scored as follows: 0 for no ankylosis, 1 for ankylosis. Again the results for the four paws are summed up and averaged for the 10 animals. Ankylosis starts to occur around day 30. During the whole treatment period, ankylosis is lower in the drug treated group than in the vehicle treated group.

TABLE 16

Ankylosis score

| Days after immunization | Vehicle | Compound 75– 100 mpk |
|---|---|---|
| 22 | 0.00 | 0.00 |
| 24 | 0.00 | 0.00 |
| 28 | 0.00 | 0.00 |
| 29 | 0.00 | 0.00 |
| 31 | 1.40 | 0.80 |
| 34 | 3.00 | 2.50 |
| 36 | 3.10 | 2.40 |
| 38 | 3.00 | 2.60 |
| 41 | 2.60 | 1.70 |
| 43 | 3.00 | 2.20 |
| 45 | 2.60 | 1.90 |
| 48 | 2.90 | 2.10 |
| 50 | 1.20 | 0.80 |

In Table 17, the incidence of ankylosis is given. No clear difference between the vehicle and drug trated groups can be observed.

TABLE 17

Incidence of ankylosis (% of animals affected)

| Days after immunization | Vehicle | Compound 75– 100 mpk |
|---|---|---|
| 22 | 0 | 0 |
| 24 | 0 | 0 |
| 28 | 0 | 0 |
| 29 | 0 | 0 |
| 31 | 90 | 60 |
| 34 | 100 | 90 |
| 36 | 100 | 90 |
| 38 | 100 | 100 |
| 41 | 80 | 70 |
| 43 | 100 | 80 |
| 45 | 80 | 80 |
| 48 | 90 | 90 |
| 50 | 40 | 40 |

In Table 18 the mean number of affected paws in the vehicle and compound treated test animals is shown; compound 75 reduces that number.

TABLE 18

Mean number of affected paws

| Days after immunization | Vehicle | Compound 75– 100 mpk |
|---|---|---|
| 22 | 0.00 | 0.00 |
| 24 | 0.00 | 0.10 |
| 28 | 2.20 | 2.40 |
| 29 | 2.50 | 2.70 |
| 31 | 2.90 | 2.80 |
| 34 | 3.00 | 2.60 |
| 36 | 3.00 | 2.20 |
| 38 | 2.90 | 2.60 |
| 41 | 3.00 | 2.40 |
| 43 | 2.70 | 2.20 |
| 45 | 2.50 | 1.90 |
| 48 | 2.50 | 1.50 |
| 50 | 1.90 | 1.20 |

In table 19, the radiographic score of the individual mice is depicted. For each paw, a score ranging from 0 (normal) to 2 (deformation of the whole paw was given. The scores of the four paws are summed up.

TABLE 19

Radiographic score of individual mice

| | Vehicle | Compound 75– 100 mpk |
|---|---|---|
| | 0.5 | 3.0 |
| | 1.5 | 4.75 |
| | 1.25 | 2.0 |
| | 5.00 | 2.5 |
| | 5.25 | 2.5 |
| | 2.5 | 1.0 |
| | 4.0 | 0.0 |
| | 7.0 | 0.0 |
| | 6.5 | 5.25 |
| | 6.5 | 2.0 |
| Average: | 4.0 | 2.3 |
| Median: | 4.5 | 2.25 |

In conclusion, oral administration of compound 75 to mice with established reduces the arthritic symptoms (paw swelling, occurrence of ankylosis and deterioration of the joints as observed on radiographs).

Example 3

*Mycobacterium butyricum*-induced Arthritis in Lewis Rats

Male SPF-breeded Lewis rats (Charles River; 225–275 g) were housed in individual cages under standard laboratory conditions (21±2° C.; 65±15% relative humidity; light-dark cycle set at 12 h). *Mycobacterium butyricum* (heat-killed and suspended in paraffin oil at 5 mg/ml; 0.05 ml) was inoculated intradermally at the tail base of the rats. On day 14 after inoculation, the diameters (Ø) of the hind paws and tibiotarsal joints ($\Sigma\emptyset14$) were compared with the initial diameters ($\Sigma\emptyset0$) and rats with a significant swelling ($\Delta\emptyset14-0 \geq 6.0$ mm) were assigned to the various treatment groups (n=6; one with a moderate, one with an intermediate, and one with a high increase).

Body weight and paw diameters were measured at days 14 and after 1-week treatment at day 21. Diet consumption was also measured and the number of dead animals on day 21 was noted. Paw swelling at day 21 was expressed as a percentage of the initial inflammation at the start of the treatment (day 14). Control animals were included in each experimental session. Test compounds were administered via a medicated diet. For that purpose, compounds were mixed with ground pellets in proportion to give an approximate daily dose. This medicated diet was administered ad libitum during the experimental period. The real dose was calculated by multiplying the consumed amount of diet with the concentration of the test compound in the diet.

Based on a frequency distribution of a series of control data (n=181), all-or-nothing criteria for drug-induced effects were established. The averaged body weight change during the 1 week experimental period in the control population was a decrease of 7 g. Only 8 out of the 186 control rats (4.3%) showed a decrease of body weight of more than 21 g, which was adopted as criterion for worsening of the Mycobacterium-induced decrease of body weight gain. Only 5 out of the 186 control rats (2.7%) showed an increase of body weight of more than 10 g, which was adopted as criterion for reversal of the Mycobacterium-induced decrease of body weight gain. In the same set of control animals, paw swelling at day 21 was on the average 117% of the initial value at day 14. Only 4 rats (2.1%) showed a percent swelling below 80%, which was adopted as criterion for anti-inflammatory activity. Sixteen control rats (8.6%) showed a percent swelling above 150%, which was adopted as a criterion for a tendency towards pro-inflammatory activity. Five control rats (2.7%) showed a percent swelling above 170%, which was adopted as a criterion for pro-inflammatory activity.

In table 20, the results obtained with different doses of compound 75 are summarized

| Dose | | % change in body-weight | | | % change in swelling | | | |
|---|---|---|---|---|---|---|---|---|
| (mg/kg) | # | #<−21% | #>10% | Mean | #<80% | #>150% | #>170% | Mean |
| 160 | 6 | 4 | 0 | −24% | 3 | 0 | 0 | 79% |
| 80 | 6 | 4 | 0 | −19% | 3 | 0 | 0 | 86% |
| 40 | 6 | 0 | 0 | −9% | 0 | 0 | 0 | 94% |

: number of animals

What is claimed is:

1. A method of treating arthropathies in a mammal comprising the step of administering a therapeutically effective amount of a farnesyl protein transferase inhibitor to said mammal wherein said farnesyl protein transferase inhibitor is a compound of formula (I), or a compound of formula (II) or (III) which is metabolized in vivo to a compound of formula (I), said compounds being represent by

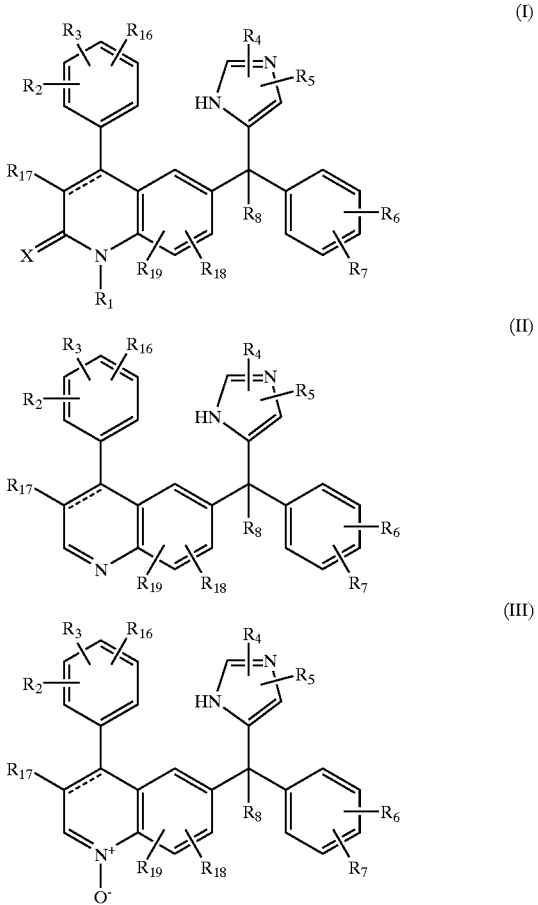

a stereoisomeric form thereof, a pharmaceutically acceptable acid or base addition salt thereof, wherein
the dotted line represents an optional bond;
X is oxygen or sulfur;
$R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di ($C_{1-6}$alkyl)amino$C_{1-6}$alkyl, amino$C_{1-6}$alkyl, or a radical of formula -Alk$^1$-C(=O)—R$^9$, -Alk$^1$-S(O)—R$^9$ or -Alk$^1$-S(O)$_2$—R$^9$, wherein
Alk$^1$ is $C_{1-6}$alkanediyl,
$R^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;
$R^2$, $R^3$ and $R^{16}$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino$C_{1-6}$alkyloxy, mono- or di($C_{1-6}$alkyl)amino$C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl, 4,4-dimethyloxazolyl; or when on adjacent positions $R^2$ and $R^3$ taken together may form a bivalent radical of formula —O—CH$_2$—O—         (a-1), —O—CH$_2$—CH$_2$—O—    (a-2)

—O—CH=CH—           (a-3)

—O—CH$_2$—CH$_2$—      (a-4)

—O—CH$_2$—CH$_2$—CH$_2$—  (a-5), or

—CH=CH—CH=CH—       (a-6);

$R^4$ and $R^5$ each independently are hydrogen, halo, $Ar^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS (O) $C_{1-6}$alkyl or $C_{1-6}$alkylS (O)$_2C_{1-6}$alkyl;

$R^6$ and $R^7$ each independently are hydrogen, halo, cyano, $C_{1-6}$alkyl, $C_{1-6}$alkyloxy, $Ar^2$oxy, trihalomethyl, $C_{1-6}$alkylthio, di ($C_{1-6}$alkyl) amino, or when on adjacent positions $R^6$ and $R^7$ taken together may form a bivalent radical of formula —O—CH$_2$—O—         (c-1), or —CH=CH—CH=CH—       (c-2);

$R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyanoc$C_{1-6}$alkyl, $C_{1-6}$alkyloxycarbonyl$C_{1-6}$alkyl, carboxy$C_{1-6}$alkyl, hydroxy$C_{1-6}$alkyl, amino$C_{1-6}$alkyl, mono- or di ($C_{1-6}$alkyl)-amino$C_{1-6}$alkyl, imidazolyl, halo$C_{1-6}$alkyl, $C_{1-6}$alkyloxy-$C_{1-6}$alkyl, aminocarbonyl$C_{1-6}$alkyl, or a radical of formula —O—$R^{10}$ (b-1), —S—$R^{10}$ (b-2), —N—$R^{11}R^{12}$ (b-3), wherein
$R^{10}$ is hydrogen, $C_{1-6}$alkyl, $C_{1-6}$alkylcarbonyl, $Ar^1$, $Ar^2C_{1-6}$alkyl, $C_{1-6}$alkyloxycarbonyl$C_{1-6}$alkyl, a radical or formula -$Alk^2$-$OR^{13}$ or -$Alk^2$-$NR^{14}R^{15}$;
$R^{11}$ is hydrogen, $C_{1-12}$alkyl, $Ar^1$ or $Ar^2C_{1-6}$alkyl;
$R^{12}$ is hydrogen, $C_{1-6}$alkyl, $C_{1-6}$alkylcarbonyl, $C_{1-6}$alkyloxycarbonyl, $C_{1-6}$alkylaminocarbonyl, $Ar^1$, $Ar^2C_{1-6}$alkyl, $C_{1-6}$alkylcarbonyl$C_{1-6}$alkyl, a natural amino acid, $Ar^1$carbonyl, $Ar^2C_{1-6}$alkylcarbonyl, amninocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical of formula -$Alk^2$-$OR^{13}$ or -$Alk^2$-$NR^{14}R^{15}$;
wherein
$Alk^2$ is $C_{1-6}$alkanediyl;
$R^{13}$ is hydrogen, $C_{1-6}$alkyl, $C_{1-6}$alkylcarbonyl, hydroxy$C_{1-6}$alkyl, $Ar^1$ or $Ar^2C_{1-6}$alkyl;
$R^{14}$ is hydrogen, $C_{1-6}$alkyl, $Ar^1$ or $Ar^2C_{1-6}$alkyl;
$R^{15}$ is hydrogen, $C_{1-6}$alkyl, $C_{1-6}$alkylcarbonyl, $Ar^1$ or $Ar^2C_{1-6}$alkyl;
$R^{17}$ is hydrogen, halo, cyano, $C_{1-6}$alkyl, $C_{1-6}$alkyloxycarbonyl, $Ar^1$;
$R^{18}$ is hydrogen, $C_{1-6}$alkyl, $C_{1-6}$alkyloxy or halo;
$R^{19}$ is hydrogen or $C_{1-6}$alkyl;
$Ar^1$ is phenyl or phenyl substituted with $C_{1-6}$alkyl, hydroxy, amino, $C_{1-6}$alkyloxy or halo; and
$Ar^2$ is phenyl or phenyl substituted with $C_{1-6}$alkyl, hydroxy, amino, $C_{1-6}$alkyloxy or halo.

2. The method of claim 1 wherein said farnesyl protein transferase inhibitor is a compound of formula (I) and wherein X is oxygen.

3. The method of claim 1 wherein said farnesyl protein transferase inhibitor is a compound of formula (I) and wherein the dotted line represents a bond.

4. The method of claim 1 wherein said farnesyl protein transferase inhibitor is a compound of formula (I) and wherein $R^1$ is hydrogen, $C_{1-6}$alkyl, $C_{1-6}$alkyloxy$C_{1-6}$alkyl or mono- or di ($C_{1-6}$alkyl)amino$C_{1-6}$alkyl.

5. The method of claim 1 wherein said farnesyl protein transferase inhibitor is a compound of formula (I) and wherein $R^3$ is hydrogen and $R^2$ is halo, $C_{1-6}$alkyl, $C_{2-6}$alkenyl, $C_{1-6}$alkyloxy, trihalomethoxy or hydroxry$C_{1-6}$alkyloxy.

6. The method of claim 1 wherein said farnesyl protein transferase inhibitor is a compound of formula (I) and wherein $R^8$ is hydrogen, hydroxy, halo$C_{1-6}$alky, hydroxy $C_{1-6}$alkyl, cyano$C_{1-6}$alkyl, $C_{1-6}$alkyloxycarbonyl$C_{1-6}$alkyl, imidazolyl, or a radical of formula —$NR^{11}R^{12}$ wherein $R^{11}$ is hydrogen or $C_{1-12}$alkyl and $R^{12}$ is hydrogen, $C_{1-6}$alkyl, $C_{1-6}$alkyloxy, $C_{1-6}$alkyloxy$C_{1-6}$alkylcarbonyl, hydroxy, or a radical of formula -$Alk^2$-$OR^{13}$ wherein $R^{13}$ is hydrogen or $C_{1-6}$alkyl.

7. The method of claim 1 wherein the compound is 4-(3-chlorophenyl)-6-[(4-chlorophenyl)hydroxy(1-methyl-1H-imidazol-5-yl)methyl]-1-methyl-2(1H)-quinolinone, 6-[amino(4-chlorophenyl)-1-methyl-1H-imidazol-5-ylmethyl]-4-(3-chlorophenyl)-1-methyl-2(1H)-quinolinone; 6-[(4-chlorophenyl)hydroxy(1-methyl-1H-imidazol-5-yl) methyl]-4-(3-ethoxy-phenyl)-1-methyl-2(1H)-quinolinone; 6-[(4-chlorophenyl)(1-methyl-1H-imidazol-5-yl)methyl]-4-(3-ethoxyphenyl)-1-methyl-2(1H)-quinolinone monohydrochloride.monohydrate; 6-[amino(4-chlorophenyl)(1-methyl-1H-imidatol-5-yl)methyl]-4-(3-ethoxyphenyl)-1-methyl-2 (1H)-quinolinone, and 6-amino(4-chlorophenyl)(1-methyl-1H-imidazol-5-yl)methyl]-1-methyl-4-(3-propylphenyl)-2 (1H -quinolinone; a stereoisomeric form thereof or a pharmaceutically acceptable acid or base addition salts thereof.

8. The method of claim 1 wherein the compound is (+)-6-[amino(4-chlorophenyl)(1-methyl-1H-imidazol-5-yl) methyl]-4-(3-chloro-phenyl)-1-methyl-2(1H)-quinolinone; or a pharmaceutically acceptable acid addition salt thereof.

9. The method of claim 1 wherein the administering step comprises administering the therapeutically effective amount of the farnesyl protein transferase inhibitor is administered orally or parenterally.

10. The method of claim 8 wherein the administring step comprises administering the farnesyl protein transferease inhibitor orally in an amount of from 100 to 1,500 mg of the compound daily, either as a single dose or subdivided into more than one dose.

11. The method of claim 1 wherein the arthropathy is rheumatoid arthritis, osteoarthritis, juvenile arthritis, polyarthritis, gout, epidemic polyarthritis (Ross River Virus infection), psoriatic arthitis, ankylosing spondylitis, systemic lupus erythematosus; or the arthropathy observed in Felty's syndrome, Reiter's syndrome or Still's syndrome.

* * * * *